United States Patent [19]

Banks

[11] Patent Number: 6,028,096
[45] Date of Patent: Feb. 22, 2000

[54] PARASITICIDAL PYRAZOLES

[75] Inventor: Bernard Joseph Banks, Sandwich, United Kingdom

[73] Assignee: Pfizer Inc, New York, N.Y.

[21] Appl. No.: 09/230,200

[22] PCT Filed: Jul. 16, 1997

[86] PCT No.: PCT/GB97/01925

§ 371 Date: Jan. 20, 1999

§ 102(e) Date: Jan. 20, 1999

[87] PCT Pub. No.: WO98/04530

PCT Pub. Date: Feb. 5, 1998

[30] Foreign Application Priority Data

Jul. 25, 1996 [GB] United Kingdom .................... 9615660
Mar. 7, 1997 [GB] United Kingdom .................... 9704775

[51] Int. Cl.[7] ...................... A61K 31/415; C07D 231/14; C07D 231/38
[52] U.S. Cl. ........................ 514/404; 514/406; 548/371.1; 548/374.1; 548/375.1
[58] Field of Search .............................. 548/371.7, 375.1, 548/374.1; 514/404

[56] References Cited

U.S. PATENT DOCUMENTS 5,232,940  8/1993  Hatton et al. .

FOREIGN PATENT DOCUMENTS 0285947   3/1988   European Pat. Off. .
19518054  12/1996  Germany .
9306089   4/1993   WIPO .

OTHER PUBLICATIONS

Farina et al., 1982, Anales de Quimica 79:333–338.
Chemical Abstracts, 1985, 102 (7):62138;.

Primary Examiner—Robert W. Ramsuer
Attorney, Agent, or Firm—Peter C. Richardson; Paul H. Ginsburg; Alan L. Koller

[57] ABSTRACT

A new group of parasiticidal pyrazoles of formula (I) wherein $R^2$ is $NH_2$, H, halogen, $NH(C_{1-6}alkyl$ optionally substituted with one or more halogen), NH(allyl optionally substituted with one or more halogen), NH(benzyl optionally substituted with one or more halogen), $NHSCF_3$, or $R^2$ is $C_{1-6}alkyl$ optionally substituted with one or more halogen; $R^3$, $R^5$ and $R^7$ are each independently H, halogen, $Sf_5$, $C_{1-6}alkyl$ optionally substituted with one or more halogen, $C_{1-6}alkoxy$ optionally substituted with one or more halogen, or $S(O)_n(C_{1-6}alkyl$ optionally substituted with one or more halogen) wherein n is 0, 1 or 2; X is O or NOY; Y is H or $C_{1-6}alkyl$ optionally substituted with one or more halogen; $R^8$ is H, $C_{1-8}alkyl$ optionally substituted with one or more halogen, or $C_{3-8}cycloalkyl$ optionally substituted by one or more halogen, or by one or more $C_{1-4}$ alkyl optionally substituted with one or more halogen, or by $C_{3-8}cycloalkylcarbonyl$; and their pharmaceutically- or veterinarily-acceptable acid addition salts are described, together with processes thereto and uses thereof.

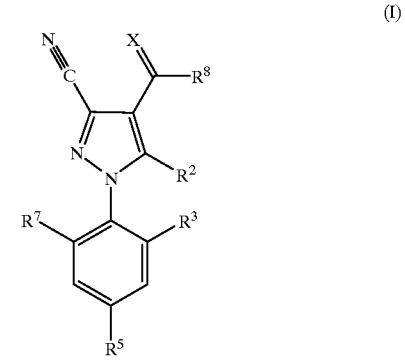

(I)

20 Claims, No Drawings

PARASITICIDAL PYRAZOLES

This invention relates to pyrazole derivatives having parasiticidal properties.

Certain parasiticidal pyrazole derivatives are already known. These include fipronil (5-amino-3-cyano-1-(2,6-dichloro-4-trifluoromethylphenyl)-4-trifluoromethylsulphinylpyrazole) and certain analogues thereof mentioned in International Patent Application WO 87/03781. Certain of the present compounds are generically disclosed in WO 87/03781, but none are specifically disclosed therein.

Farina et al describe the synthesis of 3-cyano-4-formyl-1-phenylpyrazole (*Chemical Abstracts*, vol.102(7), 62138j (1985), *An.Quim.Ser.C*(1983),79(3),333).

DE 195 18 054 A1 describes various 4-ketoxime derivatives of pyrazoles with insecticidal activity.

Kokai 8-311036 describes various 4-ketone derivatives of pyrazoles with pesticidal activity. Certain insecticidal 4-sulphurpentafluorophenylpyrazoles are disclosed in US Pat. No. 5,451,598.

A new group of parasiticidal pyrazole derivatives has now been found. Thus, according to the present invention, there is provided a compound of formula (I),

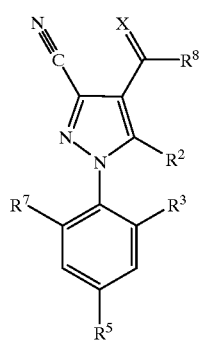

(I)

wherein $R^2$ is $NH_2$, H, halogen, $NH(C_{1-6}$ alkyl optionally substituted with one or more halogen), NH(allyl optionally substituted with one or more halogen), NH(benzyl optionally substituted with one or more halogen), $NHSCF_3$, or $R^2$ is $C_{1-6}$ alkyl optionally substituted with one or more halogen;

$R^3$, $R^5$ and $R^7$ are each independently H, halogen, $SF_5$, $C_{1-6}$ alkyl optionally substituted with one or more halogen, $C_{1-6}$ alkoxy optionally substituted with one or more halogen, or $S(O)_n(C_{1-6}$ alkyl optionally substituted with one or more halogen) wherein n is 0,1 or 2;

X is O or NOY;

Y is H or $C_{1-6}$ alkyl optionally substituted with one or more halogen;

$R^8$ is H, $C_{1-8}$ alkyl optionally substituted with one or more halogen, or $C_{3-8}$cycloalkyl optionally substituted by one or more halogen, or by one or more $C_{1-4}$ alkyl optionally substituted with one or more halogen, or by $C_{3-8}$cycloalkylcarbonyl;

with the proviso that the compound is not 3-cyano-4-formyl-1-phenylpyrazole;

or a pharmaceutically- or veterinarily-acceptable acid addition salt thereof (hereinafter referred to together as "the compounds of the invention").

The compounds of the invention are generally more efficacious or have a reduced resistance factor or have a broader spectrum of activity or are safer (e.g. less toxic) or have other more advantageous properties than the compounds of the prior art.

Pharmaceutically- and veterinarily-acceptable salts are well know to those skilled in the art, and for example include those mentioned by Berge et al, in *J.Pharm.Sci.*, 66, 1–19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, gluconate, lactate, salicylate, citrate, tartrate, ascorbate, succinate, maleate, fumarate, gluconate, formate, benzoate, methanesulphonate, ethanesulphonate, benzenesulphonate and p-toluenenesulphonate salts. Suitable base addition salts are formed from bases which form non-toxic salts and include the aluminium, calcium, lithium, magnesium, potassium, sodium, zinc and diethanolamine salts.

Alkyl and alkoxy groups may be straight- or branched-chain where the number of carbon atoms allows.

Preferably $R^2$ is $NH_2$, H, $NH(C_{1-6}$ alkly optionally substituted with one or more halogen), NH(allyl optionally substituted with one or more halogen), NH(benzyl optionally substituted with one or more halogen), $NHSCF_3$, or $R^2$ is $C_{1-6}$ alkyl optionally substituted with one or more halogen.

More preferably, $R^2$ is is H, $NHCH_3$, $NHCH_2Ph$, $NHCH_2CH=CH_2$, $NHCH(CH_3)_2$, $NHSCF_3$ or $NH_2$.

Preferably $R^3$ and $R^7$ are halogen.

More preferably, $R^3$ and $R^7$ are Cl.

Preferably $R^5$ is $SF_5$, $C_{1-6}$ alkyl optionally substituted with one or more halogen or $C_{1-6}$ alkoxy optionally substituted with one or more halogen.

More preferably $R^5$ is $OCF_3$, $CF_3$ or $SF_5$.

Preferably X is O or NOY where Y is H or $C_{1-6}$ alkyl;

More preferably X is O, NOH or $NOCH_3$.

Most preferably, X is O.

Preferably $R^8$ is H, $C_{1-8}$ alkyl optionally substituted with one or more halogen, or $C_{3-8}$cycloalkyl optionally substituted by one or more $C_{1-4}$ alkyl.

More preferably $R^8$ is H, $CH_3$, $CF_3$, $CH(CH_3)_2$, cyclobutyl, 2,2,3,3-tetramethylcyclopropyl, $C_2F_5$, $C_3F_7$, $C_2H_5$, $CF_2Cl$, $CCl_2F$ or cyclopropyl.

Particularly preferred compounds are those mentioned in the Examples.

The compounds of formula (I) where X is NOY can exist as E- or Z-geometric isomers. The present invention includes all such individual geometric isomers and mixtures thereof. The compounds of the formula (I) may possess one or more asymmetric centres and so exist in two or more stereoisomeric forms. The present invention includes all the individual stereoisomers of the compounds of formula (I) and mixtures thereof. Separation of diastereomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base.

The invention further provides Methods for the production of compounds of the invention, which are described below and in the Examples. The skilled man will appreciate that the compounds of the invention could be made by methods other than those herein described, by adaptation of the methods herein described and/or adaptation of methods known in the art, for example the art described herein.

In the Methods below, unless otherwise specified, the substituents are as defined above with reference to the compounds of formula (I) above.

Various intermediates mentioned below are also mentioned in International Patent Application publication no. WO 97/07102.

Method 1

Compounds of formula (I) where X is oxygen and $R^8$ is $CH_2R^9$, where $R^9$ is H or $C_{1-7}$alkyl optionally substituted with one or more halogen, can be made by hydration of compounds of the formula (II)

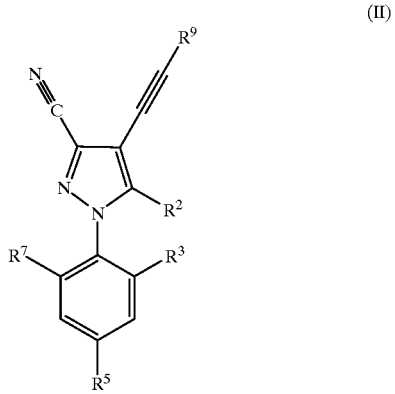

(II)

Preferably the reaction is carried out with an acid catalyst such as p-toluenesulphonic acid in a water-miscible organic solvent such as acetonitrile.

Other methods of hydrating alkynes can also be used, and will be obvious to those skilled in the art, such as those described in "Advanced Organic Chemistry", J. March, 3rd Edition, Wiley-Interscience, reaction 5-3 and the references cited therein, and suitable adaptation thereof. 4-Alkynylpyrazoles of formula (II) can be made by a coupling reaction of the corresponding 4-iodopyrazoles with an alkynyl species. For example the alkynyl species can be $R^9$—C≡CH, in which case the reaction is conveniently carried out in the presence of a $Pd^{II}$ species such as $PdCl_2(PPh_3)_2$, and CuI, in suitable solvent/base system such as N,N-dimethylformamide (DMF)/triethylamine.

Alternatively, 4-alkynylpyrazoles of formula (II) where $R^9$ is $C_{1-7}$alkyl optionally substituted with one or more halogen may be made by reaction of the corresponding 4-acetylenylpyrazoles with a $R^9$-Z species where $R^9$ is as defined above and Z is a leaving group such as Cl, Br, I, mesylate, tosylate or triflate, and a strong base such as $NaNH_2$ is used to generate the acetylide anion. Variations on this method will be obvious to those skilled in the art, such as those described in "Advanced Organic Chemistry", J. March, 3rd Edition, Wiley-Interscience, reaction 0–102 and the references cited therein, and suitable adaptation thereof.

The aforementioned 4-acetylenylpyrazoles may conveniently be prepared by reaction of the corresponding 4-iodopyrazoles with trimethylsilylacetylene in a manner analogous that described above for preparation of compounds of formula (II). The 4-trimethylsilylacetylenylpyrazole so produced can conveniently be reacted with a suitable deprotecting agent such as $K_2CO_3$, in a suitable protic solvent such as methanol. Alternatively the desilylation to produce the desired 4-acetylenylpyrazole can be carried out using a tetra-n-alkylammonium fluoride in a suitable solvent such as THF.

The 4-iodopyrazoles can be made by conventional methods known in the art, for example by reaction of the corresponding 4-unsubstituted pyrazole with a suitable iodinating species such as N-iodosuccinimide.

Method 2

All the compounds of formula (I) where X is oxygen can be made from the corresponding 4-iodopyrazoles, by reaction with a lithiating agent such as n-butyllithium, optionally in the presence of another base such as sodium hydride, optionally in the presence of cuprous bromide-dimethyl sulphide, in a suitable solvent such as tetrahydrofuran (THF), preferably at a temperature below 0° C., followed by addition of an acylating species $R^8COZ$, where Z is a suitable leaving group such as Cl, Br, I, mesylate, tosylate or triflate. Preferably,. when $R^8$ is not H, Z is $OCOR^8$, i.e. the acylating species is the relevant acid anhydride, or Z is Cl, i.e. the acylating species is the relevant acid chloride. Preferably when $R^8$ is H, the acylating species is a N,N-dialkylformamide such as DMF.

Method 3

The compounds of formula (I where X is oxygen can be made from the corresponding alcohol (III) by oxidation thereof.

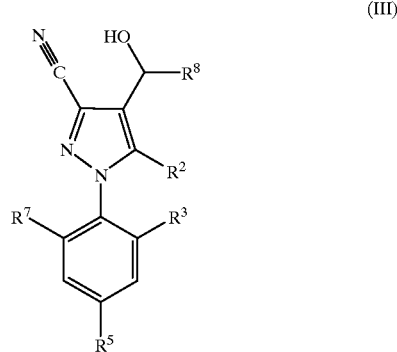

(III)

The oxidation of the alcohol (III) can be carried out with suitable oxidising systems such as those described in "Advanced Organic Chemistry", J. March, 3rd Edition, Wiley-Interscience, and the references cited therein, and suitable adaptation thereof. Conveniently, when $R^8$ is not H, the oxidation is carried out by reaction of the alcohol (III) with pyridinium chlorochromate (PCC) in dichloromethane at room temperature.

Alcohols of formula (III) where $R^8$ is not H are conveniently prepared from aldehydes of formula (I) where $R^8$ is H and X is O, by reaction with a species capable of reacting as a $(R^8)^-$ synthon, such as a suitable organometallic species, for example a Grignard reagent $R^8MgBr$. Other reagent types, such as those described in "Advanced Organic Chemistry", J. March, 3rd Edition, Wiley-Interscience, and the references cited therein, and suitable adaptation thereof, can be used.

Grignard reagents $R^8$ MgBr can be made by conventional methods such as from the appropriate optionally substituted alkyl bromide. The reactions of such aldehydes with such organometallic species is conveniently carried out in a suitable non-protic solvent, such as an ether solvent. Preferably ethers such as diethyl ether or tetrahydrofuran (THF) are used as the solvent.

Aldehydes of formula (I) where $R^8$ is H can be made by oxidative cleavage of the corresponding 4-ethenylpyrazoles of formula (IV), which in turn can be made from the corresponding alkynes of formula (II; $R^9$=H) by reduction with a suitable reducing system, or alternatively by reaction of the corresponding 4-iodopyrazoles mentioned earlier with a vinylating species such as vinyltributyltin in the presence of a $Pd^{II}$ or $Pd^0$ catalyst such as $(PPh_3)_2PdCl_2$ or $Pd(PPh_3)_4$.

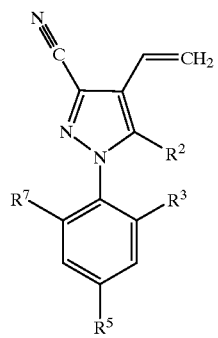

(IV)

Suitable oxidising systems for preparation of aldehydes from ethenyl compounds of formula (IV) include those mentioned in "Advanced Organic Chemistry", J. March, 3rd Edition, Wiley-Interscience, and the references cited therein, and suitable adaptation thereof. Conveniently, osmium tetroxide/sodium metaperiodate/water/acetone or osmium tetroxide/N-methylmorpholine N-oxide/sodium metaperiodate/t-butanol/water/acetone is used as the oxidising system, and the reaction is carried out at room temperature.

Method 4

All compounds of formula (I) where X is NOY can be made by condensation of the corresponding compounds of formula (I) where X is O with suitable reagents of formula $YONH_2$, or a suitable salt thereof, optionally in the presence of a suitable base such as triethylamine, pyridine or sodium acetate. Conveniently the compound of formula (I) where X is O is mixed with the hydrochloride salt of the compound of formula $YONH_2$ in pyridine and the mixture is heated to elevated temperature such as the reflux temperature of pyridine. Reagents of formula $YONH_2$, or suitable salts thereof, are available commercially or by conventional methods.

Method 5

Compounds of formula (I) where X is NOY and Y is $C_{1-6}$ alkyl optionally substituted with one or more halogen can be made by alkylation of the corresponding compounds of formula (I) where X is NOY and Y is H with a suitable optionally substituted alkylating agent, optionally in the presence of a base, using conventional methods for alkylating oximes.

Method 6

Compounds of formula (I) where $R^2$ is H can be made by reaction of the corresponding compounds of formula (I) where $R^2$ is $NH_2$ with an alkyl nitrite such as t-butyl nitrite, in a suitable solvent such as THF. Compounds of formula (I) where $R^2$ is $NH_2$ can be made by the procedures described herein.

Method 7

Compounds of formula (I) where $R^2$ is Cl, Br or I can be made by diazotisation of the corresponding compound where $R^2$ is $NH_2$ in the presence of a source of chloride, bromide or iodide. The resulting compound of formula (I) where $R^2$ is chloride, bromide or iodide can be further converted, if desired, into the corresponding compound of formula (I) where $R^2$ is F by reaction with a fluoride source such as caesium fluoride, in a suitable solvent such as DMF.

Method 8

Compounds of formula (I) where $R^2$ is $C_{1-6}$ alkyl optionally substituted with one or more halogen can be made via alkylation, with a suitable alkylating agent, of a 5-lithiopyrazole of formula (V).

The 5-lithiopyrazole (V) may be made by treatment of the corresponding 5-H pyrazole with a lithiating agent such as n-butyllithium in suitable conditions such as in an inert solvent such as THF under nitrogen. The corresponding 5-H pyrazole is in turn available from the corresponding 5-aminopyrazole by standard methods such as by adaptation of that described above in Method 6.

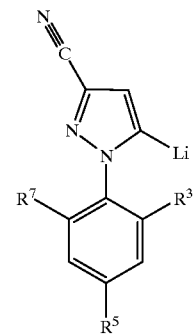

(V)

The lithium of the compound of formula (V) may be exchanged for $C_{1-6}$ alkyl optionally substituted with one or more halogen by alkylation with $(C_{1-6}$ alkyl optionally substituted with one or more halogen)-$Z^1$ where $Z^1$ is a suitable leaving group, for example iodide or mesylate.

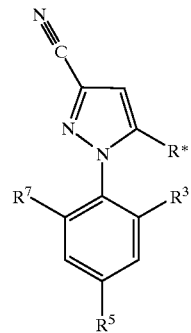

(VI)

The resulting compound of formula (VI;$R^*$=$C_{1-6}$ alkyl optionally substituted with one or more halogen) may be converted, via previously mentioned methods, such as via the corresponding 4-iodo compounds, into the compounds of formula (I) where $R^2$ is $C_{1-6}$ alkyl optionally substituted with one or more halogen.

Method 9

Compounds of formula (I) where $R^2$ is $NH(C_{1-6}$ alkyl optionally substituted with one or more halogen), NH(allyl optionally substituted with one or more halogen), NH(benzyl optionally substituted with one or more halogen) or $NHSCF_3$ can be prepared by reacting compounds of formula (I) where $R^2$ is $NH_2$ with the corresponding [($C_{1-6}$ alkyl optionally substituted with one or more halogen), (allyl optionally substituted with one or more halogen), (benzyl optionally substituted with one or more halogen) or trifluoromethylsulphenyl] halide, preferably in a polar solvent such as DMF, optionally in the presence of a base such as potassium carbonate.

Method 10

Compounds of formula (I) where X is O, $R^2$ is $NH_2$ and $R^8$ is $CF_3$ can be made by reaction, in a basic solvent such as in pyridine, of the corresponding 4-H compound with anhydrous trifluoroacetic acid.

Method 11

Where desired or necessary the compound of formula (I) is converted into a pharmaceutically or veterinarily acceptable salt thereof. A pharmaceutically or veterinarily acceptable salt of a compound of formula (I) may be conveniently be prepared by mixing together solutions of a compound of formula (I) and the desired acid or base, as appropriate. The salt may be precipitated from solution and collected by filtration, or may be collected by other means such as by evaporation of the solvent.

Compounds of the invention are available by either the methods described herein in the Methods and Examples or suitable adaptation thereof using methods known in the art. It is to be understood that the synthetic transformation methods mentioned herein may be carried out in various different sequences in order that the desired compounds can be efficiently assembled. The skilled chemist will exercise his judgement and skill as to the most efficient sequence of reactions for synthesis of a given target compound.

It will be apparent to those skilled in the art that sensitive functional groups may need to be protected and deprotected during synthesis of a compound of the invention. This may be achieved by conventional techniques, for example as described in 'Protective Groups in Organic Synthesis' by T. W. Greene and P. G. M. Wuts, John Wiley and Sons Inc, 1991.

The compounds of the invention may be separated and purified by conventional methods.

The compounds of the invention are useful because they possess parasiticidal activity in animals (including humans) and plants. They are particularly useful in the treatment of ectoparasites.

Dealing first with use of the compounds of the invention in animals (including humans), there is provided:

(a) a pharmaceutical, veterinary or agricultural parasiticidal formulation comprising a compound or salt as defined above, without proviso, in admixture with a compatible adjuvant, diluent or carrier;

(b) a compound or salt as defined above, without proviso, for use as a medicament;

(c) a method of treating a parasitic infestation at a locus, which comprises treating the locus with an effective amount of a compound or salt or composition as defined above, without proviso;

(d) a method of killing a parasite by administration of an effective amount of a compound or salt or composition as defined above, to said parasite or the vicinity thereof; and (e) the use of a compound or salt as defined above, without proviso, for the manufacture of a medicament for the treatment of a parasitic infestation.

Turning now to the use of the compounds of the invention in animals, the compounds may be administered alone or in a formulation appropriate to the specific use envisaged and to the particular species of host animal being treated and the parasite involved. The compounds may be administered orally in the form of a capsule, bolus, tablet or drench or as a pour-on or spot-on formulation, or alternatively, they can be administered by injection (e.g. subcutaneously, intramuscularly or intravenously) or as an implant.

Such formulations are prepared in a conventional manner in accordance with standard practice. Thus capsules, boluses or tablets may be prepared by mixing the active ingredient with a suitable finely divided diluent or carrier additionally containing a disintegrating agent and/or binder such as starch, lactose, talc, magnesium stearate etc. Oral drenches are prepared by dissolving or suspending the active ingredient in a suitable medium. Injectable formulations may be prepared in the form of a sterile solution which may contain other substances, for example, enough salts or glucose to make the solution isotonic with blood. Acceptable liquid carriers include the vegetable oils such as sesame oil and the like, glycerides such as triacetin and the like, esters such as benzyl benzoate, isopropyl myristate and fatty acid derivatives of propylene glycol and the like, as well as organic solvents such as pyrrolidone, glycerol formal and the like. The formulations are prepared by dissolving or suspending the active ingredient in the liquid carrier, preferably such that the final formulation contains from 0.5 to 60% by weight of the active ingredient.

These formulations will vary with regard to the weight of active compound depending on the species of host animal to be treated, the severity and type of infection and the body weight of the host. For parenteral, topical and oral administration, typical dose ranges of the active ingredient are 0.1–50 mg per kg of body weight of the animal (including humans).

As an alternative the compounds may be administered with the animal feedstuff and for this purpose a concentrated feed additive or premix may be prepared for mixing with the normal animal feed.

The compounds of the invention have utility in the control of arthropod, plant nematode, helminth or protozoan pests. The compounds of the invention may, in particular, be used in the field of veterinary medicine and livestock husbandry and in the maintenance of public health against arthropods, helminths or protozoa which are parasitic internally or externally upon vertebrates, particularly warm-blooded vertebrates, for example man and domestic animals, e.g. cattle, sheep, goats, equines, swine, poultry, dogs, cats and fish, for example Acarina, including ticks (e.g. Ixodes spp., Boophilus spp. e.g. *Boophilus microplus*, Amblyomma spp., Hyalomma spp., Rhipicephalus spp. e.g. *Rhipicephalus appendiculatus*, Haemaphysalis spp., Dermacentor spp., Ornithodorus spp. (e.g. *Ornithodorus moubata* and mites (e.g. Damalinia spp., *Dermahyssus gallinae*, Sarcoptes spp. e.g. *Sarcoptes scabiei*, Psoroptes spp., Chorioptes spp., Demodex spp., Eutrombicula spp.,) Diptera (e.g. Aedes spp., Anopheles spp., Musca spp., Hypoderma spp., Gastrophilus spp., Simulium spp.); Hemiptera (e.g. Triatoma spp.); Phthiraptera (e.g. Damalinia spp., Linoqnathus spp.) Siphonaptera (e.g. Ctenocephalides spp.); Dictyoptera (e.g. Periplaneta spp., Blatella spp.); Hymenoptera (e.g. *Mononiorium pharaonis*); for example against infections of the gastrointestinal tract caused by parasitic nematode worms, for example members of the family Trichostrongylidae, *Nippostronylus brasiliensis, Trichinella spiralis, Haemonchus contortus, Trichostronylus colubriformis, Nematodirus battus, Ostertagia circuincincta, Trichostrongylus axei,* Cooperia spp. and *Hymenolepis nana*, in the control and treatment of protozoal diseases caused by, for example Eimeria spp. e.g. *Eimeria tenella, Eimeria acervulina, Eimeria brunetti, Eimeria maxima, Eimeria necatrix, Eimeria bovis, Eimeria zuerni* and *Eimeria ovinoidalis, Trypanosoma cruzi,* Leishmania spp., Plasmodium spp., Babesia spp., Trichomonadidae spp., Histomonas spp., Giardia spp., Toxoplasma spp., *Entamoeba histolytica* and Theileria spp.; in the protection of stored products, for example cereals, including grain and flour, groundnuts, animal foodstuffs, timber and household goods, e.g. carpets and textiles, against attack by arthropods, more especially beetles, including weevils, moths and mites, for example Ephestia spp. (flour moths), Anthrenus spp. (carpet beetles), Tribolium spp. (flour beetles), Sitophilus spp. (grain weevils) and Acarus spp. (mites), in the control of cockroaches, ants and termites and similar arthropod pests in infested domestic and industrial premises and in the control of mosquito larvae in waterways, wells, reservoirs or other running or standing water; for the treatment of foundations, structure and soil in the prevention of the attack on buildings by termites, for example, Reticulitermes spp., Heterotermes spp., Coptoterms spp.; in agriculture, against adults, larvae and eggs of Lepidoptera (butterflies and moths), e.g. Heliothis spp. such as *Heliothis virescens* (tobacco budworm), *Heliothis armioera* and Heliothis zea, Spodoptera spp. such as *S. exempta, S. littoralis* (Egyptian cotton worm), *S. eridania* (southern army worm), *Mamestra configurata* (bertha army worm); Earias spp. e.g. *E. insulana* (Egyptian bollworm), Pectinophora spp. e.g. *Pectinophora gossypiella* (pink bollworm), Ostrinia spp. such as *O. nubilalis* (European cornborer), *Trichoplusia ni* (cabbage looper), Pieris spp. (cabbage worms), Laphyqma spp. (army worms), Agrotis and Amathes spp. (cutworms), Wiseana spp. (porina moth), Chilo spp. (rice stem borer), Tryporyza spp. and Diatraea spp. (sugar cane borers and rice borers), *Sparganothis pilleriana* (grape berry moth), *Cydia pomonella* (codling moth), Archips spp. (fruit tree tortrix moths), *Plutella xylostella* (diamond black moth); against adult and larvae of Coleoptera (beetles) e.g. *Hypothenemus hampei* (coffee berry borer), Hylesinus spp. (bark beetles), *Anthonomus grandis* (cotton boll weevil), Acalymma spp. (cucumber beetles), Lema spp., Psylliodes spp., *Leptinotarsa decemlineata* (Colorado potato beetle), Diabrotica spp. (corn rootworms), Gonocephalum spp. (false wire worms), Agriotes spp. (wireworms), Dermolepida and Heteronychus spp. (white grubs), *Phaedon cochleariae* (mustard beetle), *Lissorhoptrus oryzophilus* (rice water weevil), Melioethes spp. (pollen beetles), Ceutorhynchus spp., Rhynchophorus and Cosmopolites spp. (root weevils); against Hemiptera e.g. Psylla spp., Bemisia spp., Trialeurodes spp., Aphis spp., Myzus spp., *Megoura viciae,* Phylloxera spp., Adelges spp., *Phorodon humnuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseucoccus spp., Helopeltis spp. (mosquito bugs), Lygus spp., Dysdercus spp., Oxycarenus spp., Nezara spp.; Nymenoptera e.g. Athalia spp. and Cephus spp. (saw flies), Atta spp. (leaf cutting ants); Diptera e.g. Hylemyia spp. (root flies), Atherigona spp. and Chlorops spp. (shoot flies), Phytomyza spp. (leaf miners), Ceratitis spp. (fruit flies); Thysanoptera such as *Thrips tabaci*: Orthoptera such as Locusta and Schistocerca spp. (locusts) and crickets e.g. Gryllus spp. and Acheta spp.; Collembola e.g. Sminthurus spp. and Onychiurus spp. (springtails), Isoptera e.g. Odontotermes spp. (termites), Derrnaptera e.g. Forficula spp. (earwigs) and also other arthropods of agricultural significance such as Acari (mites) e.g. Tetranychus spp., Panonychus spp. and Bryobia spp. (spider mites), Eriophyes spp. (gall mites), Polyphacotarsonemus spp.; Blaniulus spp. (millipedes), Scutigerella spp. (symphilids), Oniscus spp. (woodlice) and Triops spp. (crustacea); nematodes which attack plants and trees of importance to agriculture, forestry and horticulture either directly or by spreading bacterial, viral, mycoplasma or fungal diseases of the plants, root-knot nematodes such as Meliodogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*); lesion nematodes such as Pratylenchus spp. (e.g. *P. pratensis*); Belonoliamus spp. (e.g. *B. gracilis*); Tylenchulus spp. (e.g. *T semipenetrans*); Rotylenchulus spp. (e.g. *R. reniformis*); Rotylenchus spp. (e.g. *R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T. primitivus*); dagger nematodes such as Xiphinema spp. (e.g. *X diversicaudatum*), Longidorus spp. (e.g. *L. elongatus*); Hoplolaimus spp. (e.g. *H. coronatus*); Aphelenchoides spp. (e.g. *A. ritzema-bosi, A. besseyi*); stem and bulb eelworms such as Ditylenchus spp. (e.g. *D. dipsaci*).

The compounds of the invention also have utility in the control of arthropod or nematode pests of plants. The active compound is generally applied to the locus in which arthropod or nematode infestation is to be controlled at a rate of about 0.1 kg to about 25 kg of active compound per hectare of locus treated. Under ideal conditions, depending on the pest to be controlled, the lower rate may offer adequate protection. On the other hand, adverse weather conditions, resistance of the pest and other factors may require that the active ingredient be used in higher proportions. In foliar application, a rate of 1 g to 1000 g/ha may be used.

When the pest is soil-borne, the formulation containing the active compound is distributed evenly over the area to be treated in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The compounds of the invention may be applied in solid or liquid compositions to the soil principally to control those nematodes dwelling therein but also to the foliage principally to control those nematodes attacking the aerial parts of the plants (e.g. Aphelenchoides spp. and Ditylenchus spp. listed above).

The compounds of the invention are of value in controlling pests which feed on parts of the plant remote from the point of application, e.g. leaf feeding insects are killed by the subject compounds applied to roots. In addition the compounds may reduce attacks on the plant by means of antifeeding or repellent effects.

The compounds of the invention are of particular value in the protection of field, forage, plantation, glasshouse, orchard and vineyard crops, or ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g. Urocerus) or beetles (e.g. scolytids, platypodids, lyctids, bostrychids, cerambycids, anobiuds), or termites, for example, Reticulitermes spp., Heterotermes spp., Coptotermes spp.

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

The compounds of the invention are of value in the control or arthropods, helminths or protozoa which are injurious to, or spread or act as vectors of diseases in man and domestic animals, for example those hereinbefore mentioned, and more especially in the control of ticks, mites, lice, fleas, midges and biting, nuisance and myiasis flies. The compounds of the invention are particularly useful in controlling arthropods, helminths or protozoa which are present inside domestic host animals or which feed in or on the skin or suck the blood of the animal, for which purpose they may be administered orally, parenterally, percutaneously or topically.

Coccidiosis, a disease caused by infections by protozoan parasites of the genus Eimeria, is an important potential cause of economic loss in domestic animals and birds, particularly those raised or kept under intensive conditions. For example, cattle, sheep, pigs and rabbits may be affected, but the disease is especially important in poultry, in particular chickens.

The poultry disease is generally spread by the birds picking up the infectious organism in droppings on contaminated litter or ground or by way of food or drinking water. The disease is manifested by hemorrhage, accumulation of blood in the ceca, passage of blood to the droppings, weakness and digestive disturbances. The disease often terminates in the death of the animal but the fowl which survive severe infections have their market value substantially reduced as a result of the infection.

Administration of a small amount of a compound of the invention preferably by combination with poultry feed is effective in preventing or greatly reducing the incidence of coccidiosis. The compounds are effective against both the cecal form (caused by E. tenella) and the intestinal forms (principally caused by E. acervulina, E. brunetti, E. maxima and E. necatrix).

The compounds of the invention also exert an inhibitory effect on the oocysts by greatly reducing the number and or the sporulation of those produced.

Therefore, according to a further aspect of the invention, there is provided a parasiticidal formulation comprising a compound of the invention, in admixture with a compatible adjuvant, diluent or carrier. Preferably, the formulation is adapted for topical administration.

The invention further provides a compound of the invention for use as a parasiticide; and a method of treating a parasitic infestation at a locus, which comprises treatment of the locus with an effective amount of a compound of the invention. Preferably, the locus is the skin or fur of a human or non-human animal, or the surface or vicinity of a plant.

It is to be appreciated that reference to treatment includes prophylaxis as well as the alleviation of established symptoms of a parasitic infestation.

Test for Insecticidal Activity

Adult flies (Stomoxys calcitrans) are collected and anaesthetized using $CO_2$. 1 μl of an acetone solution containing the test compound is applied directly to the thorax of the fly. Flies are then placed carefully into a 50 ml tube covered with damp gauze to recover from the $CO_2$. Negative controls have 1 μl of acetone dispensed onto them. Mortality is assessed 24 hours after dosing.

The following data illustrate the efficacy of the compounds of the invention in comparison with certain of the compounds (MB-cpd) disclosed in WO 87/03781. The figures in the last column are the dosages required to give 100% mortality in the above test. The compounds in the Table below have the formula:

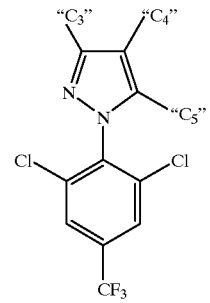

| Compound | C-3 | C-4 | C-5 | μg/fly |
|---|---|---|---|---|
| Example A4 | CN | $COCH_3$ | $NH_2$ | 0.05 |
| Example A5 | CN | $COCH_3$ | H | 0.01 |
| Example A11 | CN | $CH{=}NOCH_3$ | $NH_2$ | 0.05 |
| MB-cpd 107 | $CF_3$ | $COCH_3$ | H | 0.5 |
| MB-cpd 2 | CN | CN | $NH_2$ | >0.1 |

The invention is illustrated by the following Examples.

EXAMPLES & PREPARATIONS

Melting points were determined using a Gallenkamp melting point apparatus and are uncorrected. Nuclear magnetic resonance (NMR) data were obtained using a Bruker AC300 or AM300 and are quoted in parts per million from tetramethylsilane. Mass spectral data were obtained on a Finnigan Mat. TSQ 7000 or a Fisons Instruments Trio 1000. The calculated and observed ions quoted refer to the isotopic composition of lowest mass. Reference to "ether" in this section should be read as diethyl ether, unless specified otherwise. HPLC purification was performed on a 21×250 Dynamax™ 5 μ ODS reverse-phase column eluted at 10 ml/minute with acetonitrile:0.005M aqueous heptanesulphonic acid:methanol (50:40:10). Fractions were processed by evaporation of the non-aqueous components followed by partition between ether and saturated aqueous sodium hydrogen carbonate solution. The organic layer was then separated, dried and evaporated.

Preparation A1

5-Amino-3-cyano-1-(2,6-dichloro-4-trifluoromethylphenyl)-4-iodopyrazole

To a stirred solution of 5-amino-3-cyano-1-(2,6-dichloro-4-trifluoromethylphenyl)pyrazole (5.0 g) in acetonitrile (60 ml) at room temperature was added N-iodosuccinimide (3.52 g), portionwise over a period of five minutes. Stirring was continued for 1 hr and the mixture was then evaporated to dryness to provide the crude product (8.2 g), still containing succinimide. This may be used without further purification or, if desired, purified by partitioning between dichloromethane and water, separating, drying (MgSO$_4$) and evaporating the organic layer to produce a yellow solid. Trituration with hexane provides the title compound as a white solid, m.p. 213° C. (decomp.).

Preparation A2

5-Amino-3-cyano-1-(2,6-dichloro-4-trifluoromethNlphenyl)-4-trimethylsilylethynylpyrazole To a stirred solution of 5-amino-3-cyano-1-(2,6-dichloro-4-trifluoromethylphenyl)-4-iodopyrazole (6.96 g, crude from example A1) in triethylamine (30 ml) and dimethylformamide (6 ml) at room temperature was added trimethylsilylacetylene (3 ml), cuprous iodide (150 mg) and bis(triphenylphosphine)palladium(II) chloride (300 mg). The mixture was heated at 50–60° C. for one hour, trimethylsilylacetylene (0.3 ml) was then added and stirring and heating continued for a further period of 30 minutes. The cooled reaction mixture was diluted with water (250 ml) extracted with ether (250 ml). The organic layer was separated (aided by the addition of brine). The aqueous layer was re-extracted with ether (250 ml). The combined ether extracts were dried (MgSO$_4$) and evaporated to give the crude product as a gum (4.67 g).

Purification by column chromatography on silica gel eluted with dichloromethane:hexane (1:1) followed by recrystallisation from ether/hexane provided the title compound as a white solid, m.p. 181–182° C.

NMR(CDCl$_3$): 0.2 (s, 9H), 4.1 (br. s, 2H), 7.7 (s, 2H).

MS (thermospray): M/Z [M+NH$_4$]434.2; C$_{16}$H$_{13}$Cl$_2$F$_3$N$_4$Si+NH$_4$ requires 434.0.

Preparation A3

5-Amino-3-cyano-1-(2,6-dichloro-4-trifluoromethylphenyl)-4-ethynylpyrazole

To a stirred solution of 5-amino-3-cyano-1-(2,6-dichloro-4-trifluoromethylphenyl)-4-trimethylsilylethynylpyrazole (2.0 g, crude from example 2) in methanol (30 ml) was added potassium carbonate (1 g). After 10 minutes at room temperature the reaction mixture was partitioned between ether (100 ml) and water (100 ml). The organic layer was separated, washed with brine (100 ml), dried (MgSO$_4$) and evaporated. The residue was purified by column chromatography on silica gel eluted with dichloromethane followed by recrystallisation from ether to provide the title compound as a white solid, m.p. 215–216° C.

NMR(CDCl$_3$): 3.49 (s, 1H), 4.2 (br. s, 2H), 7.8 (s, 2H)

MS (thermospray): M/Z [M+NH$_4$]362.4; C$_{13}$H$_5$Cl$_2$F$_3$N$_4$+NH$_4$ requires 362.0.

Example A4

4-Acetyl-5-amino-3-cyano-1-(2,6-dichloro-4-trifluoromethylphenyl)pyrazole

To a solution of 5-amino-3-cyano-1-(2,6-dichloro-4-trifluoromethylphenyl)-4-ethynylpyrazole (0.345 g) in acetonitrile (5 ml) was added p-toluenesulphonic acid (0.5 g) and the mixture was stirred at room temperature for 2 hours and then poured into water (100 ml) and ether (100 ml). The organic layer was separated, washed with saturated aqueous sodium hydrogen carbonate solution (50 ml), brine (50 ml), dried (Na$_2$SO$_4$) and evaporated. The residue was purified by column chromatography on silica gel (40 g) eluted with dichloromethane:hexane (10:1). Combination and evaporation of suitable fractions gave the title compound as a white crystalline solid, m.p. 200–1° C.

NMR(CDCl$_3$): 2.65 (s, 3H), 5.83 (br. s, 2H), 7.82 (s, 2H).

MS (thermospray): M/Z [M+NH$_4$]380.4; C$_{13}$H$_7$Cl$_2$F$_3$N$_4$O+NH$_4$ requires 380.03.

Example A5

4-Acetyl-3-cyano-1-(2,6-dichloro-4-trifluoromethylphenyl)pyrazole

To a stirred solution of 4-acetyl-5-amino-3-cyano-1-(2,6-dichloro-4-trifluoromethylphenyl)pyrazole (0.4 g) in tetrahydrofuran (2 ml) was added dropwise t-butylnitrite (0.0262 ml). The mixture was heated under reflux for 30 minutes. The reaction mixture was applied to a silica gel (1 g) column and eluted with tetrahydrofuran to provide the title compound as white solid, m.p. 166–168° C.

NMR(CDCl$_3$): 2.67 (s, 3H), 7.8 (s, 2H), 8.12 (s, 1H).

MS (thermospray): M/Z [M+NH$_4$]365.0; C$_{13}$H$_6$Cl$_2$F$_3$N$_3$O+NH$_4$ requires 365.02.

Example A6

5-Amino-3-cyano-1-(2,6-dichloro-4-trifluoromethylphenyl)-4-(1-oximinoethyl)pyrazole To a stirred solution of 4-acetyl-5-amino-3-cyano-1-(2,6-dichloro-4-trifluoromethylphenyl)pyrazole (0.25g) in pyridine (5 ml) was added hydroxylamine hydrochloride (0.05 g). After stirring at room temperature for 6 hours the mixture was heated at 50° C. for 3 hours, after which it was evaporated. The residue was taken up in ether and washed with aqueous citric acid solution (1M), water, then dried and evaporated. The residue was crystallised from propan-2-ol/hexane and further purified by column chromatography on silica gel eluted with dichloromethane. Combination and evaporation of suitable fractions gave the title compound as a tan solid, m.p. 105–110° C.

NMR(CDCl$_3$): 2.62 & 2.68 (s+s, 3H), 5.02 (br. s, 1H), 5.82 (br. s, 2H), 7.8 & 7.82 (s+s, 2H).

MS (thermospray) M/Z [M+NH$_4$]395.9; C$_{13}$H$_8$Cl$_2$F$_3$N$_5$O+NH$_4$ requires 395.04.

Example A7

5-Amino-3-cyano-1-(2,6-dichloro-4-trifluoromethylphenyl)-4-(1-methoximinoethyl)pyrazole To a stirred solution of 4-acetyl-5-amino-3-cyano-1-(2,6-dichloro-4-trifluoromethylphenyl)pyrazole (0.25 g) in pyridine (5 ml) was added methoxylamine hydrochloride (0.086 g). The mixture was heated under reflux for 3 hours, then cooled and diluted with ether (100 ml). The solution was washed with aqueous citric acid solution (1M), saturated aqueous sodium hydrogen carbonate solution (50 ml), brine (50 ml), then dried and evaporated. The residue was purified by column chromatography on silica gel eluted with dichloromethane, then dichloromethane: methanol (99:1). Combination and evaporation of suitable fractions gave the title compound as a white solid, m.p. 214–216° C.

NMR(CDCl$_3$): 2.4 (s, 3H), 3.94 (s, 3H), 5.28 (br. s, 2H), 7.79 (s, 2H).

MS (thermospray): M/Z [M+H]391.9; C$_{14}$H$_{10}$Cl$_2$F$_3$N$_5$O+H requires 392.03.

Preparation A8

5-Amino-3-cyano-1-(2,6-dichloro-4-trifluoromethylphenyl)-4-ethenylpyrazole

To a stirred solution of 5-amino-3-cyano-1-(2,6-dichloro-4-trifluoromethylphenyl)-4-iodopyrazole (2 g) in dimethylformamide (10 ml) at room temperature was added vinyltri-n-butyl tin (4.25 g) and tetra-kis-triphenylphosphinepalladium(0) (0.3 g). The mixture was heated at 75° C. for one hour and then cooled and left at room temperature for 60 hours. The reaction mixture was diluted with water and extracted with ether. The organic layer was separated, washed with brine, dried (MgSO$_4$) and evaporated to give the crude product as a black oil (6 g) which was purified by column chromatography on silica gel (200 g) eluted with dichloromethane:hexane (1:1). Combination and evaporation of appropriate fractions gave the title compound as a buff solid, m.p. 186–70° C.

NMR(CDCl$_3$): 3.85 (s, 2H), 5.41 (d, 1H), 5.7 (d, 1H), 6.52 (dd, 1H), 7.8 (s,2H)

MS (thermospray): M/Z [M+H]347.0; C$_{13}$H$_7$Cl$_2$F$_3$N$_4$+H requires 347.0.

Example A9

5-Amino-3-cyano-1-(2,6-dichloro-4-trifluoromethylphenyl)-4-formylpyrazole

To a stirred solution of 3-cyano-1-(2,6-dichloro-4-trifluoromethylphenyl)-4-ethenylpyrazole (0.1 g) in acetone (9 ml) was added water (1 ml), osmium tetroxide (0.1 ml of a 2.5% soultion in t-butanol) and then sodium metaperiodate (0.136 g, in three portions over 5 minutes). After 1 hour sodium metaperiodate (0.136 g) was added and after a further 30 minutes the reaction mixture was filtered and the filtrate evaporated. The residue was partitioned between water and dichloromethane. The organic layer was separated, dried and evaporated. The residue was purified by column chromatography on silica gel eluted with dichloromethane. After combination and evaporation of suitable fractions the residue was crystallised from propan-2-ol/water to give the title compound as a white solid, m.p. 194–197° C.

NMR(CDCl$_3$): 5.7 (br. s, 2H), 7.84 (s, 2H), 9.9 (s, 1H).

MS (thermospray): M/Z [M+NH$_4$]366.5; C$_{12}$H$_5$Cl$_2$F$_3$N$_4$O+NH$_4$ requires 366.01.

Example A10

5-Amino-3-cyano-1-(2,6-dichloro-4-trifluoromethylphenyl)-4-oximinomethylpyrazole To a stirred solution of 5-amino-3-cyano-1-(2,6-dichloro-4-trifluoromethylphenyl)-4-formylpyrazole (0.25 g) in ethanol (3 ml) was added hydroxylamine hydrochloride (0.075 g), sodium acetate (0.1 g) and water (0.1 ml). After stirring at room temperature overnight the mixture was evaporated. The residue was taken up in ether and washed with water, then brine, then dried and evaporated. The residue was crystallised from propan-2-ol/water and further purified by column chromatography on silica gel eluted with dichloromethane then dichloromethane:methanol (99:1). After combination and evaporation of suitable fractions the residue was further purified by column chromatography on silica gel eluted with ether. Combination and evaporation of suitable fractions gave the title compound as a white solid, m.p. 175–178° C.

NMR(CDCl$_3$): 5.09 (br. s, 2H), 7.05 (s, 1H), 7.82 (s, 2H), 8.25 (s, 1H).

MS (thermospray): M/Z [M+H]364.2; C$_{12}$H$_6$Cl$_2$F$_3$N$_5$O+H requires 364.0.

Example A11

5-Amino-3-cyano-1-(2,6-dichloro-4-trifluoromethylphenyl)-4-methoximinomethylpyrazole To a stirred solution of 5-amino-3-cyano-1-(2,6-dichloro-4-trifluoromethylphenyl)-4-formylpyrazole (0.07 g) in pyridine (2 ml) was added methoxylamine hydrochloride (0.025 g). The mixture was heated at 90° C. for 1.5 hours, then cooled and diluted with ether. The solution was washed with aqueous citric acid solution (1M), saturated aqueous sodium hydrogen carbonate solution, brine, then dried and evaporated. The residue was purified by recrystallisation from propan-2-ol to give the title compound as a white solid, m.p. 208–210° C.

NMR(CDCl$_3$): 3.97 (s, 3H), 5.11 (br. s, 2H), 7.8 (s, 2H), 8.19 (s, 1H).

MS (thermospray): M/Z [M+H]377.7; C$_{13}$H$_8$Cl$_2$F$_3$N$_5$O+H requires 378.0.

Example A14

5-Amino-3-cyano-1-(2,6-dichloro-4-trifluoromethylphenyl)-4-trifluoroacetylpyrazole To a stirred solution of 5-amino-3-cyano-1-(2,6-dichloro-4-trifluoromethylphenyl)-4-iodopyrazole (6 g) in anhydrous tetrahydrofuran (50 ml) at −5° C. was added sodium hydride (1.07 g of a 60% dispersion in mineral oil). The mixture was stirred for 10 minutes then cooled to −70° C. n-Butyllithium (5.637 ml of a 2.5M solution in hexanes) was added dropwise at such a rate as to maintain the temperature below −65° C. After a further 30 minutes cuprous bromide dimethyl sulphide complex (2.765 g) was added and the mixture warmed to −30° C. over a period of 1.5 hours. It was then cooled to −65° C. and trifluoroacetic anhydride (5.68 ml) added dropwise at such a rate as to maintain the temperature below −65° C. The reaction mixture was then allowed to warm to room temperature over a period of 2 hours and saturated aqueous ammonium chloride solution (150 ml) added The mixture was extracted with ethyl acetate (100 ml, x2). The combined organic layers were washed with saturated aqueous sodium hydrogen carbonate solution (50 ml, x2), dried and evaporated. The residue was purified by column chromatography on silica gel (400 g) eluted with hexane:dichloromethane (80:20) changing incrementally to dichloromethane and then, again incrementally to dichloromethane:ethyl acetate (50:50). Combination and evaporation of suitable fractions was followed by further purification by reverse phase high performance chromatography on C18 silica eluted with methanol:0.005M PIC B7 buffer (60:40). Appropriate fractions were combined and evaporated. Their residue was partitioned between ether and saturated aqueous sodium hydrogen carbonate solution. The organic layer was separated, dried and evaporated to give the title compound as a pale orange solid, m.p. 226° C.

NMR(CDCl$_3$): 6.1 (br. s, 2H), 7.86 (s, 2H).

MS (thermospray): M/Z [M+NH$_4$]433.7; C$_{13}$H$_4$Cl$_2$F$_6$N$_4$O+NH$_4$ requires 434.0.

Preparation A15

3-Cyano-1-(2,6-dichloro-4-trifluoromethylphenyl)-4-iodopyrazole

To a stirred solution of 5-amino-3-cyano-1-(2,6-dichloro-4-trifluoromethylphenyl)-4-iodopyrazole (90 g) in tetrahydrofuran (720 ml) heated to 65° C. was added t-butylnitrite (144 ml) over a period of 0.5 hours. Stirring and heating were continued for 3 hours. The cooled reaction mixture was evaporated and the residue recrystallised from propanol to give the title compound as a white solid, m.p. 83–4° C.

NMR(CDCl$_3$): 7.7 (s, 1H), 7.79 (s, 2H).

MS (thermospray): M/Z [M+NH$_4$]448.8; C$_{11}$H$_3$Cl$_2$F$_3$N$_3$I+NH$_4$ requires 448.9.

Preparation A16

3-Cyano-1-(2,6-dichloro-4-trifluoromethylphenyl)-4-ethenylpyrazole

A solution of 3-cyano-1-(2,6-dichloro-4-trifluoromethylphenyl)-4-iodopyrazole (58 g) in dimethylformamide (350 ml) containing vinyltri-n-butyltin (116 ml) and tetrakis(triphenylphosphine)palladium(0) (3.5 g,) was stirred at 75° C. for 3 hours. The reaction mixture was poured into water (600 ml) and ether (600 ml). The organic layer was separated, washed with water (×5), brine (700 ml), dried (Na$_2$SO$_4$) and evaporated. The residue was recrystallised from propan-2-ol to give the title compound as a pale brown solid, m.p.75–6° C.

NMR(CDCl$_3$): 5.5 (d, 1H), 5.94 (d, 1H), 6.64 (dd, 1H), 7.64 (s, 1H), 7.77 (s, 2H).

MS (thermospray) M/Z [M+NH$_4$]349.5; C$_{13}$H$_6$Cl$_2$F$_3$N$_3$+NH$_4$ requires 349.02.

Example A17

3-Cyano-1-(2,6-dichloro-4-trifluoromethylphenyl)-4-formylpyrazole

A solution of 3-cyano-1-(2,6-dichloro-4-trifluoromethylphenyl)-4-ethenylpyrazole (0.1 g), N-methylmorpholine oxide (0.005 g), osmium tetroxide (50 μl of a 2.5% solution in t-butanol) in water (5 ml) and acetone (45 ml) was stirred at room temperature for 16 hours Sodium metaperiodate (0.005 g) was added and stirring continued for 16 hours. The reaction mixture was evaporated and the residue partititoned between ether and saturated aqueous sodium hydrogen carbonate solution. The aqueous layer was separated and extracted with ether. The combined ether extracts were dried (Na$_2$SO$_4$) and evaporated. The residue was purified by column chromatography on silica gel (5 g) eluted with dichloromethane. Combination and evaporation of suitable fractions gave the title compound as a biege solid, m.p. 167.5–168.5° C.

NMR(CDCl$_3$): 7.8 (s, 2H), 8.18 (s, 1H), 10.08 (s, 1H).

MS (thermospray): M/Z [M+NH$_4$]351.3; C$_{12}$H$_4$Cl$_2$F$_3$N$_3$O+NH$_4$ requires 351.0.

Example A18

3-Cyano-1-(2,6-dichloro-4-trifluoromethylphenyl)-4-oximinomethylpyrazole

A mixture of 3-cyano-1-(2,6-dichloro-4-trifluoromethylphenyl)-4-formylpyrazole (0.4 g), hydroxylamine hydrochloride (0.4 g), tetrahydrofuran (5 ml), methanol (50 ml) and water (2.5 ml) were stirred overnight. The mixture was partitioned between ether (50 ml) and water. The organic layer was separated, washed with saturated aqueous sodium hydrogen carbonate solution (50 ml), water (50 ml), then dried over Na$_2$SO$_4$ and evaporated to provide the title compound as a white solid, m.p. 170° C.

NMR(CDCl$_3$): 7.54&7.86 (s+s,1H), 7.79 (s, 2H), 8.15&8.79 (br. s+br. s, 1H), 8.2&8.6 (s+s,1H).

MS (thermospray): M/Z [M+NH$_4$]366.3; C$_{12}$H$_5$Cl$_2$F$_3$N$_4$O+NH$_4$ requires 366.01.

Example A19

3-Cyano-1-(2,6-dichloro-4-trifluoromethylphenyl)-4-(2-methylpropanoyl)pyrazole

To a stirred solution of 3-cyano-1-(2,6-dichloro-4-trifluoromethylphenyl)-4-acetylpyrazole (0.69 g) in tetrahydrofuran (10 ml) at 0° C. under an atmosphere of nitrogen was added portionwise potassium t-butoxide (0.2444 g) followed after 5 minutes by methyl iodide (0.121 ml). After stirring for a further 30 minutes the reaction mixture was poured into water (100 ml) and ether (100 ml). The organic layer was separated, dried (MgSO$_4$) and evaporated to give a oil which was purified by column chromatography on silica gel (20 g) eluted with dichloromethane:hexane (4:1). Combination and evaporation of suitable fractions gave the title compound as a white solid, m.p. 168–169° C.

NMR(CDCl$_3$): 1.2 (d, 6H), 3.32 (h, 1H), 7.8 (s, 2H), 8.13 (s, 1H).

MS (thermospray): M/Z [M+NH$_4$]393.7; C$_{15}$H$_{10}$Cl$_2$F$_3$N$_3$O+NH$_4$ requires 393.1.

Example A20

3-Cyano-4-cyclopropylcarbonyl-1-(2,6-dichloro-4-trifluoromethylphenyl)pyrazole

To a stirred solution of 3-cyano-1-(2,6-dichloro-4-trifluoromethylphenyl)-4-iodopyrazole (0.22 g) in tetrahydrofuran (5 ml) at −78° C. under an atmosphere of nitrogen was added, at such a rate that the temperature of the reaction mixture did not exceed −65° C., n-butyllithium (0.21 ml of a 2.5M solution in hexanes). After stirring for a further 5 minutes cyclopropanecarbonyl chloride (0.13 ml) was added and the mixture allowed to warm to room temperature. The reaction mixture was poured into saturated aqueous sodium hydrogen carbonate solution (5 ml) and extracted twice with ether (25 ml). The combined organic layers were washed with water (50 ml), dried (Na$_2$SO$_4$) and evaporated to give a brown oil which was purified by column chromatography on silica gel (40 g) eluted with dichloromethane. Combination and evaporation of suitable fractions gave the title compound as a white solid, m.p. 195–197° C.

NMR(CDCl$_3$): 1.17 (m, 2H), 1.36 (m, 2H), 2.54 (m, 1H), 7.8 (s, 2H), 8.17 (s, 1H).

MS (thermospray): M/Z [M+NH$_4$]391.5; C$_{15}$H$_8$Cl$_2$F$_3$N$_3$O+NH$_4$ requires 391.0.

Example A21

3-Cyano-1-(2,6-dichloro-4-trifluoromethylphenyl)-4-trifluoroacetylpyrazole

To a stirred solution of 3-cyano-1-(2,6-dichloro-4-trifluoromethylphenyl)-4-iodopyrazole (4.62 g) in tetrahydrofuran (100 ml) at −75° C. under an atmosphere of nitrogen was added, at such a rate that the temperature of the reaction mixture did not exceed −75° C., n-butyllithium (4.7 ml of a 2.5M solution in hexanes). A solution of methyl trifluoroacetate (1.93 ml) in tetrahydrofuran (5 ml) was then added at such a rate that the temperature of the reaction mixture did not exceed −75° C. Upon completion of the addition the mixture was allowed to warm to room temperature. Water (100 ml) was added and the mixture extracted twice with ethyl acetate (80 ml). The combined organic layers were dried ($Na_2SO_4$) and evaporated to give a brown gum which was purified by column chromatography on silica gel (250 g) eluted with dichloromethane. Combination and evaporation of suitable fractions gave the title compound as a pale yellow solid, m.p. 124–125° C.

NMR($CDCl_3$): 7.83 (s, 2H), 8.3 (s, 1H).

MS (thermospray): M/Z [M+H]401.7; $C_{13}H_3Cl_2F_6N_3O$+H requires 401.96.

Example A22

3-Cyano-1-(2,6-dichloro-4-trifluoromethylphenyl)-4-(2,2,2-trifluoro-1-methoximinoethyl)pyrazole A solution of 3-cyano-1-(2,6-dichloro-4-trifluoromethylphenyl)-4-trifluoroacetylpyrazole (0.3 g) and methoxylamine hydrochloride (0.068 g) in anhydrous pyridine (1 ml) was heated under gentle reflux for two hours and then left overnight at room temperature. The mixture was diluted with ether (20 ml) and extracted with citric acid (20 ml of a 1M aqueous solution). The organic layer was separated and washed with saturated aqueous sodium hydrogen carbonate solution (20 ml), then dried ($Na_2SO_4$) and evaporated to provide a pale orange solid which was purified by column chromatography on silica gel (10 g) eluted with a mixture of dichloromethane:hexane (1:1). Combination and evaporation of suitable fractions gave the title compound as a pale yellow solid, m.p. 104–105° C.

NMR($CDCl_3$): 4.23 (s, 3H), 7.8 (s, 2H), 7.84 (m) & 7.98 (s) together 1H.

MS (thermospray): M/Z [M+$NH_4$]448.1; $C_{14}H_6Cl_2F_6N_4O$+$NH_4$ require 448.02.

Examples A23 and A24

3-Cyano-4-cyclobutylcarbonyl-1-(2,6-dichloro-4-trifluoromethylphenyl)pyrazole and 3-Cyano-4-(2-cyclobutylcarbonylcyclobutylcarbonyl)-1-(2,6-dichloro-4-trifluoromethylphenyl)pyrazole To a stirred solution of 3-cyano-1-(2,6-dichloro-4-trifluoromethylphenyl)-4-iodopyrazole (0.75 g) in tetrahydrofuran (15 ml) at −78° C. under an atmosphere of nitrogen was added, at such a rate that the temperature of the reaction mixture did not exceed −78° C., n-butyllithium (0.72 ml of a 2.5M solution in tetrahydrofuran). Once the addition was complete cyclobutylcarbonyl chloride (0.81 ml) was added and the mixture allowed to warm to room temperature and then partitioned between ether (50 ml) and saturated aqueous sodium hydrogen carbonate solution (50 ml). The organic layer was separated, washed with water, dried ($Na_2SO_4$) and evaporated. The residue was purified by column chromatography on silica gel eluted with dichloromethane:hexane (1:4). Combination and evaporation of suitable fractions gave the title compounds.

NMR($CDC_3$): 2.0 (m, 1H), 2.1 (m, 1H), 2.4 (m, 4H), 3.9 (m, 1H), 7.8 (s, 2H), 8.09 (s, 1H).

MS (thermospray): M/Z [M+H]388.0; $C_{16}H_{10}Cl_2F_3N_3O$+H requires 388.02.

and

NMR($CDCl_3$): 1.79 (m, 1H), 1.94 (m, 5H), 2.1 (m, 2H), 2.7 (m, 4H), 3.4 (m, 1H), 7.8 (s, 2H),7.9 (s, 1H).

MS (thermospray): M/Z [M+H]470.1; $C_{21}H_{16}Cl_2F_3N_3O_2$+H requires 470.06.

Example A25

3-Cyano-1-(2,6-dichloro-4-trifluoromethylphenyl)-4-(2,2,3,3-tetramethylcyelopropylcarbonyl)pyrazole To a stirred solution of 3-cyano-1-(2,6-dichloro-4-trifluoromethylphenyl)-4-iodopyrazole (0.75 g) in tetrahydrofuran (15 ml) at −78° C. under an atmosphere of nitrogen was added, at such a rate that the temperature of the reaction mixture did not exceed −70° C., n-butyllithium (0.76 ml of a 2.5M solution in tetrahydrofuran). Once the addition was complete 2,2,3,3-tetramethylcyclopropanecarbonyl chloride (1.39 g) was added. The mixture maintained at −78° C. for 15 minutes, then allowed to warm to room temperature and partitioned between ether (100 ml) and saturated aqueous sodium hydrogen carbonate solution (100 ml). The organic layer was separated, washed with water, dried ($Na_2SO_4$) and evaporated. The residue was purified by column chromatography on silica gel eluted with dichloromethane:hexane (2:1). Combination and evaporation of suitable fractions gave the title compound.

NMR($CDCl_3$): 1.2 (s, 6H), 1.3 (s, 6H), 1.95 (s, 1H), 7.7 (s, 2H), 7.75 (s, 1H).

MS (thermospray): M/Z [M+H]430.0; $C_{19}H_{16}Cl_2F_3N_3O$+H requires 430.07.

Example A26

3-Cyano-1-(2,6-dichloro-4-trifluoromethylphenyl)-4-pentafluoropropanoylpyrazole

To a stirred solution of 3-cyano-1-(2,6-dichloro-4-trifluoromethylphenyl)-4-iodopyrazole (3.0 g) in tetrahydrofuran (80 ml) at −80° C. under an atmosphere of nitrogen was added, at such a rate that the temperature of the reaction mixture did not exceed −73° C., n-butyllithium (2.78 ml of a 2.5M solution in hexanes). The mixture was stirred at −73° C. for 10 minutes and then a solution of methyl pentafluoropropionate (0.89 ml) in tetrahydrofuran (5 ml) was then added at such a rate that the temperature of the reaction mixture did not exceed −75° C. Upon completion of the addition the mixture allowed to warm to room temperature over a period of 1.5 hours. Water (100 ml) was added and the mixture extracted twice with ethyl acetate (80 ml). The combined organic layers were dried ($Na_2SO_4$) and evaporated to give a pale yellow solid which was purified by column chromatography on silica gel (150 g) eluted with dichloromethane:hexane (9:1). Combination and evaporation of suitable fractions gave a yellow oil which was further purified by column chromatography on silica gel (50 g) eluted with dichloromethane:hexane (9:1). Combination and evaporation of suitable fractions gave the title compound as a white solid, m.p. 120° C.

NMR($CDCl_3$): 7.8 (s, 2H), 8.2 (s, 1H).

MS (thermospray): M/Z [M+$NH_4$]468.9; $C_{14}H_3Cl_2F_8N_3O$+$NH_4$ requires 468.99.

Example A27

3-Cyano-1-(2,6-dichloro-4-trifluoromethylphenyl)-4-heptafluorobutanoylpyrazole

To a stirred solution of 3-cyano-1-(2,6-dichloro-4-trifluoromethylphenyl)-4-iodopyrazole (3.0 g) in tetrahydrofuran (80 ml) at −80° C. under an atmosphere of nitrogen was added, at such a rate that the temperature of the reaction mixture did not exceed −73° C., n-butyllithium (2.78 ml of a 2.5M solution in hexanes). The mixture was stirred at −73° C. for 10 minutes and then a solution of methyl heptafluorobutyrate (1.07 ml) in tetrahydrofuran (5 ml) was then added at such a rate that the temperature of the reaction mixture did not exceed −75° C. Upon completion of the addition the mixture allowed to warm to room temperature over a period of 1.5 hours. Water (100 ml) was added and the mixture extracted twice with ethyl acetate (50 ml). The combined organic layers were dried ($Na_2SO_4$) and evaporated to give a pale yellow solid which was purified by column chromatography on silica gel (150 g) eluted with ether:hexane (3:2). Combination and evaporation of suitable fractions gave a yellow oil which was further purified by column chromatography on silica gel (150 g) eluted initially with hexane:ether (19:1), then hexane:ether (9:1) and finally hexane:ether (1:1). Combination and evaporation of suitable fractions gave the title compound as a pale yellow solid, m.p. 102–103° C.

NMR($CDCl_3$): 7.8 (s, 2H), 8.2 (s, 1H).

MS (thermospray): M/Z [M+$NH_4$]518.7; $C_{15}H_3Cl_2F_{10}N_3O$+$NH_4$ requires 518.99.

Example A30

3-Cyano-1-(2,6-dichloro-4-trifluoromethylphenyl)-4-propanoylpyrazole

To a stirred solution of 3-cyano-1-(2,6-dichloro-4-trifluoromethylphenyl)-4-iodopyrazole (7.2 g) in tetrahydrofuran (80 ml) at −78° C. under an atmosphere of nitrogen was added, at such a rate that the temperature of the reaction mixture did not exceed −71° C., n-butyllithium (8 ml of a 2.5M solution in hexanes). A solution of methyl propionate (3.2 ml) in tetrahydrofuran (10 ml) was then added at such a rate that the temperature of the reaction mixture did not exceed −72° C. Upon completion of the addition the mixture was stirred at −72° C. and then allowed to warm to room temperature over a period of 1.5 hours. After stirring overnight at room temperature water (100 ml) was added and the mixture extracted twice with ethyl acetate (200 ml). The combined organic layers were dried ($Na_2SO_4$) and evaporated to give a brown gum which was purified by column chromatography on silica gel (500 g) eluted with dichloromethane. Combination and evaporation of suitable fractions gave a brown solid which was further purified by column chromatography on silica gel (60 g) eluted with dichloromethane. Combination and evaporation of suitable fractions gave the title compound as a pale yellow solid, m.p. 143° C.

NMR($CDCl_3$): 1.28 (t, 3H), 3.0 (q, 2H), 7.8 (s, 2H), 8.15 (s, 1H).

MS (thermospray): M/Z [M+$NH_4$]379.3; $C_{14}H_8Cl_2F_3N_3O$+$NH_4$ requires 379.03.

Preparation A31

5-Amino-3-cyano-1-(2,6-dichloro-4-trifluoromethylphenyl)-4-(prop-1-ynyl)pyrazole To a stirred solution of 5-amino-3-cyano-1-(2,6-dichloro-4-trifluoromethylphenyl)-4-iodopyrazole (0.904 g) in dimethylformamide (2 ml) and triethylamine (10 ml) contained in a stainless steel bomb was added cuprous iodide (60 mg) and bis(triphenylphosphine)palladium(II) chloride (120 mg). The reaction vessel was cooled to −78° C. and propyne (2 g) condensed into it. The vessel was sealed and then heated at 70° C. for 18 hours and then left at room temperature for 2 days. The reaction mixture was partitioned between ether and water. The organic layer was separated, washed with brine, dried ($MgSO_4$) and evaporated. The residue was purified by column chromatography on silica gel eluted with dichloromethane:hexane (1:1) to provide the title compound as a white solid m.p. 226–8° C.

NMR($CDCl_3$): 2.2 (s, 3H), 4.19 (br. s, 2H), 7.78 (s, 2H)

MS (thermospray): M/Z [M+H]358.9; $C_{14}H_7Cl_2F_3N_4$+H requires 359.0

Example A32

5-Amino-3-cyano-1-(2,6-dichloro-4-trifluoromethylphenyl)-4-propanoylpyrazole

To a stirred solution of 5-amino-3-cyano-1-(2,6-dichloro-4-trifluoromethylphenyl)-4-(prop-1-ynyl)pyrazole (2.1 g) in acetonitrile (40 ml) was added p-toluenesulphonic acid monohydrate (292 g) and the mixture was stirred at room temperature for 1 hour. p-Toluenesulphonic acid monohydrate (1 g) was then added and stirring continued overnight. Acetonitrile (20 ml) was added p-toluenesulphonic acid monohydrate (1 g) were added and stirring continued for 1 hour and then the reaction mixture was poured into saturated aqueous sodium hydrogen carbonate solution (500 ml) and extracted twice with ether (100 ml). The organic layer was separated, washed with brine (100 ml), dried ($Na_2SO_4$) and evaporated. The residue was purified by column chromatography on silica gel (70 g) eluted with dichloromethane. Combination and evaporation of suitable fractions gave the title compound as a pale brown solid, m.p. 167–169° C.

NMR($CDCl_3$): 1.26 (t, 3H), 3.03 (q, 2H), 5.83 (br.s, 2H), 7.8 (s, 2H).

MS (thermospray): M/Z [M+H]377.2; $C_{14}H_9Cl_2F_3N_4O$+H requires 377.02.

Preparation B1

5-Amino-3-cyano-1-(2,6-dichloro-4-sulphurpentafluorophenyl)-4-iodopyrazole

To a stirred solution of 5-amino-3-cyano-1-(2,6-dichloro-4-sulphurpentafluorophenyl)pyrazole (18.95 g) in acetonitrile (100 ml) at room temperature was added N-iodosuccinimide (11.5 g) in four portions over a period of five minutes. After 15 minutes the mixture was evaporated to dryness and the residual solid was treated with dichloromethane and water. The insoluble material was filtered off and dissolved in ethyl acetate. The solution was dried ($Na_2SO_4$) and evaporated to provide the title compound as a buff solid, m.p. 253° C.

NMR($CDCl_3$): 3.94 (br. s, 2H), 7.92 (s, 2H)

MS (thermnospray): M/Z [M+$NH_4$]521.9; $C_{10}H_4Cl_2F_5IN_4S$+$NH_4$ requires 521.88.

Preparation B2

5-Amino-3-cyano-1-(2,6-dichloro-4-sulphurpentafluorophenyl)-4-trimethylsilylethynylpyrazole To a stirred solution of 5-amino-3-cyano-1-(2,6-dichloro-4-sulphurpentafluorophenyl)-4-iodopyrazole (5.05 g) in dimethylformnamide (5 ml) at room temperature was added cuprous iodide (0.1 g), bis(triphenylphosphine)palladium (II) chloride (0.2 g), trimethylsilylacetylene (2.9 ml) and triethylamine (1 ml). The mixture was heated at 70° C. for 5 hours. The cooled reaction mixture was allowed to stand at room temperature overnight and then poured into water. The precipitate was filtered off and taken up in dichloromethane (50 ml). Following the addition of hexane (100 ml) an oil separated. The supernatant was evaporated to give the crude product which was purified by column chromatography on silica gel (80 g) eluted with dichloromethane-:hexane (1:9 then 2:8). Combination and evaporation of suitable fractions followed by recrystallisation of their residue from di-isopropyl ether/hexane provided the title compound as a white microcrystalline solid, m.p. 175° C.

NMR(CDCl$_3$): 0.29 (s, 9H), 4.19 (br. s, 2H), 7.94 (s, 2H)

MS (thermospray): M/Z [M+NH$_4$]492.1; C$_{15}$H$_{13}$Cl$_2$F$_5$N$_4$SSi+NH$_4$ requires 492.02.

Preparation B3

5-Amino-3-cyano-1-(2,6-dichloro-4-sulphurpentafluorophenyl)-4-ethynylpyrazole

To a stirred solution of 5-amino-3-cyano-1-(2,6-dichloro-4-sulphurpentafluorophenyl)-4-trimethylsilylethynylpyrazole (0.4 g) in dichloromethane (5 ml) was added tetra-n-butylammonium fluoride (1.5 ml of a 1M solution in tetrahydrofuran). After one hour tetra-n-butylammonium fluoride (0.5 ml of a 1M solution in tetrahydrofuran) was added. After three hours the reaction mixture was evaporated to dryness. The residue was purified by column chromatography on silica gel (6.6 g) eluted with hexane:ethyl acetate (9:1, then 4:1, then 2:1) and then ethyl acetate. Combination and evaporation of suitable fractions followed by recrystallisation of their residue from ethyl acetate/hexane provided the title compound as a yellow microcrystalline solid, m.p. 251° C.

NMR(d$_6$-DMSO): 3.31 (s, 1H), 6.88 (br. s, 2H), 8.47 (s, 2H)

MS (thermospray): M/Z [M+H]403.0; C$_{12}$H$_5$Cl$_2$F$_5$N$_4$S+H requires 402.96.

Example B4

4-Acetyl-5-amino-3-cyano-1-(2,6-dichloro-4-sulphurpentafluorophenyl)-pyrazole

To a solution of 5-amino-3-cyano-1-(2,6-dichloro-4-sulphurpentafluorophenyl)-4-ethynylpyrazole (0.06 g) in acetonitrile (1.5ml) was added p-toluenesulphonic acid (0.085 g) and the mixture was stirred at room temperature for 2 hours. Saturated aqueous sodium hydrogen carbonate solution (5 ml) and ethyl acetate (5 ml) were added. The organic layer was separated, dried (Na$_2$SO$_4$) and evaporated onto silica gel (0.5 g). The residue was purified by column chromatography on silica gel (5 g) eluted with hexane/ethyl acetate mixtures. Combination and evaporation of suitable fractions gave a yellow solid which was further purified by reverse phase high performance chromatography on C18 silica eluted with acetonitrile:water:methanol (60:30:10). Appropriate fractions were combined and evaporated to give the title compound as a white solid, m.p. 272–273° C.

NMR(CDCl$_3$): 2.5 (s, 3H), 7.5 (br. s, 2H), 8.5 (s, 2H).

MS (thermospray): M/Z [M+NH$_4$]437.9; C$_{12}$H$_7$Cl$_2$F$_5$N$_4$OS+NH$_4$ requires 438.0.

Example B5

4-Acetyl-3-cyano-1-(2,6-dichloro-4-sulphurpentafluorophenyl)pyrazole

To a stirred solution of 4-acetyl-5-amino-3-cyano-1-(2,6-dichloro-4-sulphurpentafluorophenyl)pyrazole (0.5g) in tetrahydrofuran (10 ml) heated under reflux was added dropwise a solution of t-butylnitrite (0.85 ml) in tetrahydrofuran (2.5 ml). The mixture was heated for 2 hours and then evaporated. The residue was triturated with di-isopropyl ether and left to stand overnight. The precipitate so obtained was filtered off and recrystallised from propan-2-ol to provide the title compound as an off-white solid, m.p. 158° C.

NMR(CDCl$_3$): 2.67 (s, 3H), 7.94 (s, 2H), 8.12 (s, 1H).

MS (thermospray): M/Z [M+NH$_4$]423.2; C$_{12}$H$_6$Cl$_2$F$_5$N$_3$OS+NH$_4$ requires 422.99.

Preparation C1

5-Amino-3-cyano-1-(2,6-dichloro-4-trifluoromethoxyphenyl)-4-iodopyrazole

To a stirred solution of 5-amino-3-cyano-1-(2,6-dichloro-4-trifluoromethoxyphenyl)pyrazole (4.17 g) in acetonitrile (20 ml) at room temperature was added N-iodosuccinimide (2.79 g). After 15 minutes the mixture was evaporated to dryness and the residual orange solid was taken up in dichloromethane. The solution was washed with water, then brine, then dried (Na$_2$SO$_4$) and evaporated to provide the title compound as a pale orange solid, m.p. 149.5–150.0° C.

NMR(CDCl3): 3.95 (br. s, 2H), 7.41 (s, 2H)

MS (thermospray): M/Z [M+H]463.1; C$_{11}$H$_4$Cl$_2$F$_3$IN$_4$O+H requires 462.88

Preparation C2

5-Amino-3-cyano-1-(2,6-dichloro-4-trifluoromethoxyphenyl)-4-trimethylsilylethynylpyrazole To a stirred solution of 5-amino-3-cyano-1-(2,6-dichloro-4-trifluoromethoxyphenyl)-4-iodopyrazole (5.489 g) in dimethylformamide (4 ml) at room temperature was added trimethylsilylacetylene (3.35 ml), cuprous iodide (0.116 g), bis(triphenylphosphine)palladium(II) chloride (0.228 g) and triethylamine (1 ml). The mixture was heated at 60° C. for 2.5 hours. Trimethylsilylacetylene (1.675 ml), cuprous iodide (0.058 g) and bis(triphenylphosphine)palladium(II) chloride (0.114 g) were then added and stirring and heating was continued for a further period of one hour. The cooled reaction mixture was diluted with water and extracted with ether. The ether extract was dried (MgSO$_4$) and evaporated to give the crude product which was purified by column chromatography on silica gel eluted with dichloromethane/hexane. Combination and evaporation of suitable fractions followed by recrystallisation of their residue from dichloromethane/hexane provided the title compound as a pale yellow solid, m.p. 151.5–152.1° C.

NMR(CDCl$_3$): 0.26 (s, 9H), 4.15 (br. s, 2H), 7.42 (s, 2H)

MS (thermospray): M/Z [M+H]433.7; C$_{16}$H$_{13}$Cl$_2$F$_3$N$_4$OSi+H requires 433.03.

Preparation C3

5-Amino-3-cyano-1-(2,6-dichloro4-trifluoromethoxyphenyl)-4-ethynylpyrazole

To a stirred solution of 5-amino-3-cyano-1-(2,6-dichloro-4-trifluoromethoxyphenyl)-4-trimethylsilylethynylpyrazole (0.4657 g) in dichloromethane (5 ml) cooled in an ice-water bath was slowly added tetra-n-butylamntmonium fluoride (1.07 ml of a 1M solution in tetrahydrofuran). After five minutes the ice-water bath was removed. Stirring was continued for ten minutes then the reaction mixture was washed with water. The aqueous layer was washed with dichloromethane. The combined organic layers were washed with brine, dried (Na$_2$SO$_4$) and evaporated to provide the title compound as an oily solid which upon drying in an oven crystallised to a white solid, m.p. 175.7–176.1° C.

NMR(CDCl$_3$): 3.48 (s, 1H), 4.2 (br. s, 2H), 7.42 (s, 2H)

MS (thermnospray): M/Z [M+NH$_4$]377.9; C$_{13}$H$_5$Cl$_2$F$_3$N$_4$O+NH$_4$ requires 378.01.

Example C4

4-Acetyl-5-amino-3-cyano-1-(2,6-dichloro-4-trifluoromethoxyphenyl)pyrazole

To a solution of 5-amino-3-cyano-1-(2,6-dichloro-4-trifluoromethoxyphenyl)-4-ethynylpyrazole (0.318 g) in acetonitrile (10 ml) was added p-toluenesulphonic acid (0.455 g) and the mixture was stirred at room temperature for 1.5 hours and then evaporated to dryness. The residue was taken up in ether and washed with saturated aqueous sodium hydrogen carbonate solution (5 ml). The aqueous layer was twice extracted with ether. The combined organic layers were dried (Na$_2$SO$_4$) and evaporated. The residue was purified by column chromatography on silica gel eluted with hexane:ether (1:1). Combination and evaporation of suitable fractions gave a yellow solid which was further purified by reverse phase high performance chromatography on C18 silica eluted with acetonitrile:water:methanol (60:30:10). Appropriate fractions were combined and evaporated to give, after recrystallisation from propan-2-ol, the title compound as a white solid, m.p. 192.3–192.7° C.

NMR(CDCl$_3$): 2.68 (s, 3H), 5.85 (br. s, 2H), 7.44 (s, 2H).

MS (thermospray): M/Z [M+NH$_4$]396.3; C$_{13}$H$_7$Cl$_2$F$_3$N$_4$O$_2$+NH$_4$ requires 396.02.

Example C5

4-Acetyl-3-cyano-1-(2,6-dichloro-4-trifluoromethoxyphenyl)pyrazole

To a stirred solution of 4-acetyl-5-amino-3-cyano-1-(2,6-dichloro-4-trifluoromethoxyphenyl)pyrazole (0.302 g) in tetrahydrofuran (10 ml) at 2° C. was added t-butylnitrite (0.66 ml). The mixture was heated under reflux for 1.5 hours and then evaporated. The residue was purified by column chromatography on silica gel eluted with dichloromethane. Combination and evaporation of suitable fractions provided the title compound as a white solid, m.p. 105.7–106.6° C.

NMR(CDCl$_3$): 2.66 (s, 3H), 7.41 (s, 2H), 8.1 (s, 1H).

MS (thermospray): M/Z [M+NH$_4$]380.9; C$_{13}$H$_6$Cl$_2$F$_3$N$_3$O$_2$+NH$_4$ requires 381.01.

Example D1

3-Cyano-1-(2,6-dichloro-4-trifluoromethylphenyl)-5-methylamino-4-trifluoroacetylpyrazole To a stirred solution of 5-amino-3-cyano-1-(2,6-dichloro-4-trifluoromethylphenyl)-4-trifluoroacetylpyrazole (1 g) in anhydrous N,N-dimethylformamide (5 ml) at room temperature was added potassium carbonate (0.69 g), then iodomethane (97 µl). The mixture was stirred at room temperature for one hour. Water (30 ml) was then added, and the mixture was extracted with ether (50 ml, ×2). The combined organic layers were washed with water (30 ml, ×2), and evaporated. The residue was purified by column chromatography on silica gel (50 g) eluted with dichloromethane. Combination and evaporation of suitable fractions gave the title compound as a white solid, m.p 160–161° C.

NMR(CDCl$_3$): 2.64 (d, 3H), 7.80 (s, 2H), 8.09 (br.s, 1H).

MS (thermospray): M/Z [M+NH$_4$]447.8; C$_{14}$H$_6$Cl$_2$F$_6$N$_4$O+NH$_4$ requires 448.0.

Example D2

3-Cyano-1-(2,6-dichloro-4-trifluoromethylphenyl)-5-(prop-2-enylamino)-4-trifluoroacetylpyrazole To a stirred solution of 5-amino-3-cyano-1-(2,6-dichloro-4-trifluoromethylphenyl)-4-trifluoroacetylpyrazole (1 g) in anhydrous N,N-dimethylformamide (4 ml) at room temperature was added potassium carbonate (0.7 g), then allyl bromide (165 µl). The mixture was stirred at room temperature for 40 minutes. Water (50 ml) was then added, and the mixture was extracted with ether (50 ml, ×2). The combined organic layers were washed with water (50 ml), dried (Na$_2$SO$_4$), filtered and evaporated. The residue was purified by column chromatography on silica gel (50 g) eluted with dichloromethane. Combination and evaporation of suitable fractions gave the title compound as a very pale yellow/white solid, m.p 115–116° C.

NMR(CDCl$_3$): 3.51 (m, 2H), 5.10 (dd, 1H), 5.18 (dd, 1H), 5.64 (m, 1H), 7.78 (s, 2H), 8.21 (br.s, 1H).

MS (thermospray): M/Z [M+NH$_4$]474.0; C$_{16}$H$_8$Cl$_2$F$_6$N$_4$O+NH$_4$ requires 474.0.

Example D3

3-Cyano-1-(2,6-dichloro-4-trifluoromethylphenyl)-5-phenylmethylamino-4-trifluoroacetylpyrazole To a stirred solution of 5-amino-3-cyano-1-(2,6-dichloro-4-trifluoromethylphenyl)-4-trifluoroacetylpyrazole (1 g) in anhydrous N,N-dimethylformamide (4 ml) at room temperature was added potassium carbonate (0.7 g), then benzyl bromide (228 µl). The mixture was stirred at room temperature for 40 minutes. Water (50 ml) was then added, and the mixture was extracted with ether (50 ml, ×2). The combined organic layers were washed with water (50 ml), dried (Na$_2$SO$_4$), filtered and evaporated. The residue was purified by column chromatography on silica gel (50 g) eluted with dichloromethane. Combination and evaporation of suitable fractions gave the title compound as a white solid, m.p 75–76° C.

NMR(CDCl$_3$): 4.13 (d, 2H), 6.95 (dd, 2H), 7.26(m, 3H), 7.62 (s, 2H), 8.54 (br.s, 1H).

MS (thermospray): M/Z [M+NH$_4$]523.7; C$_{20}$H$_{10}$Cl$_2$F$_6$N$_4$O+NH$_4$ requires 524.0.

Example D4

3-Cyano-1-(2,6-dichloro-4-trifluoromethylphenyl)-5-(prop-2-ylamino)-4-trifluoroacetylpyrazole To a stirred solution of 5-amino-3-cyano-1-(2,6-dichloro-4-trifluoromethylphenyl)-4-trifluoroacetylpyrazole (1 g) in anhydrous N,N-dimethylformmamide (4 ml) at room temperature was added potassium carbonate (0.7 g), then 2-iodopropane (190 µl). The mixture was stirred at room temperature for 48 hours. Water (50 ml) was then added, and the mixture was extracted with ether (50 ml, ×2). The combined organic layers were washed with water (50 ml), dried (Na$_2$SO$_4$) filtered and evaporated. The residue was purified by column chromatography on silica gel (50 g) eluted with dichloromethane. Combination and evaporation of suitable fractions gave the title compound as a very pale yellow solid, m.p 136–137° C.

NMR(CDCl$_3$): 1.13 (d, 6H), 3.13 (m, 1H), 7.79 (s, 2H), 8.09 (br.d, 1H).

MS (thermospray): M/Z [M+NH$_4$]475.9; C$_{16}$H$_{10}$Cl$_2$F$_6$N$_4$O+NH$_4$ requires 476.0.

Preparation 1

5-Amino-3-cyano-1-(2,6-dichloro-4-trifluoromethylphenyl)pyrazole, used in Preparation A1, was prepared as described in EP-295,117-A1.

Preparation 2

5-Amino-3-cyano-1-(2,6-dichloro-4-sulphurpentafluorophenyl)pyrazole, used in Preparation B1, was prepared as described in International Patent Application WO 93/06089.

Preparation 3

5-amino-3-cyano-1-(2,6-dichloro-4-trifluoromethoxyphenyl)pyrazole, used in preparation C1, was prepared as described in ep-295,117-A1.

I claim:

1. A compound of formula (I),

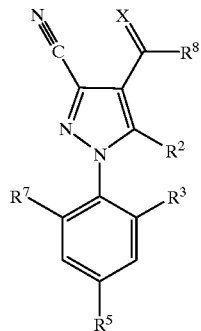

(I)

wherein

R$^2$ is NH$_2$, H, halogen, NH(C$_{1-6}$ alkyl optionally substituted with one or more halogen), NH(allyl optionally substituted with one or more halogen), NH(benzyl optionally substituted with one or more halogen), NHSCF$_3$, or R$^2$ is C$_{1-6}$ alkyl optionally substituted with one or more halogen;

R$^3$, R$^5$ and R$^7$ are each independently H, halogen, SF$_5$, C$_{1-6}$ alkyl optionally substituted with one or more halogen, C$_{1-6}$ alkoxy optionally substituted with one or more halogen, or S(O)$_n$(C$_{1-6}$ alkyl optionally substituted with one or more halogen) wherein n is 0, 1 or 2;

X is O or NOY;

Y is H or C$_{1-6}$ alkyl optionally substituted with one or more halogen;

R$^8$ is H, C$_{1-8}$ alkyl optionally substituted with one or more halogen, or C$_{3-8}$ cycloalkyl optionally substituted by one or more halogen, or by one or more C$_{1-4}$ alkyl optionally substituted with one or more halogen, or by C$_{3-8}$ cycloalkylcarbonyl;

with the proviso that the compound is not 3-cyano-4-formyl-1-phenylpyrazole;

or a pharmaceutically- or veterinarily-acceptable acid addition salt thereof.

2. A compound or salt according to claim 1 wherein R$^2$ is NH$_2$, H, halogen, NH(C$_{1-6}$ alkyl optionally substituted with one or more halogen), NH(allyl optionally substituted with one or more halogen), NH(benzyl optionally substituted with one or more halogen), NHSCF$_3$, or R$^2$ is C$_{1-6}$ alkyl optionally substituted with one or more halogen.

3. A compound or salt according to claim 1 wherein R$^3$ and R$^7$ are halogen.

4. A compound or salt according to claim 1 wherein R$^5$ is SF$_5$, C$_{1-6}$ alkyl optionally substituted with one or more halogen or C$_{1-6}$ alkoxy optionally substituted with one or more halogen.

5. A compound or salt according to claim 1 wherein X is O or NOY where Y is H or C$_{1-6}$ alkyl.

6. A compound or salt according to claim 1 wherein R$^8$ is H, C$_{1-8}$ alkyl optionally substituted with one or more halogen, or C$_{3-8}$ cycloalkyl optionally substituted by one or more C$_{1-4}$ alkyl.

7. A compound or salt according to claim 1 wherein R$^2$ is H, NHCH$_3$, NHCH$_2$Ph, NHCH$_2$CH=CH$_2$, NHCH(CH$_3$)$_2$, NHSCF$_3$ or NH$_2$.

8. A compound or salt according to claim 1 wherein R$^3$ and R$^7$ are Cl.

9. A compound or salt according to claim 1 wherein R$^5$ is OCF$_3$, CF$_3$ or SF$_5$.

10. A compound or salt according to claim 1 wherein X is O, NOH or NOCH$_3$.

11. A compound or salt according to claim 1 wherein R$^8$ is H, CH$_3$, CF$_3$, CH(CH$_3$)$_2$, cyclobutyl, 2,2,3,3-tetramethylcyclopropyl, C$_2$F$_5$, C$_3$F$_7$, C$_2$H$_5$, CF$_2$Cl, CCl$_2$F or cyclopropyl.

12. A compound or salt according to claim 1 wherein X is O.

13. A compound or salt according to claim 1 selected from:

4-acetyl-5-amino-3-cyano-1-(2,6-dichloro-4-trifluoromethylphenyl)pyrazole;

4-acetyl-3-cyano-1-(2,6-dichloro-4-trifluoromethylphenyl)pyrazole;

5-amino-3-cyano-1-(2,6-dichloro-4-trifluoromethylphenyl)-4-(1-oximinoethyl)pyrazole;

5-amino-3-cyano-1-(2,6-dichloro-4-trifluoromethylphenyl)-4-(1-methoximinoethyl)pyrazole;

5-amino-3-cyano-1-(2,6-dichloro-4-trifluoromethylphenyl)-4-methoximinomethylpyrazole;

5-amino-3-cyano-1-(2,6-dichloro-4-trifluoromethylphenyl)-4-trifluoroacetylpyrazole;

3-cyano-1-(2,6-dichloro-4-trifluoromethylphenyl)-4-oximinomethylpyrazole;

3-cyano-1-(2,6-dichloro-4-trifluoromethylphenyl)-4-(2-methylpropanoyl)pyrazole;

3-cyano-4-cyclopropylcarbonyl-1-(2,6-dichloro-4-trifluoromethylphenyl)pyrazole;

4-acetyl-5-amino-3-cyano-1-(2,6-dichloro-4-sulphurpentafluorophenyl)pyrazole;

4-acetyl-3-cyano-1-(2,6-dichloro-4-sulphurpentafluorophenyl)pyrazole;

4-acetyl-5-amino-3-cyano-1-(2,6-dichloro-4-trifluoromethoxyphenyl)pyrazole;

4-acetyl-3-cyano-1-(2,6-dichloro-4-trifluoromethoxyphenyl)pyrazole;

3-cyano-1-(2,6-dichloro-4-trifluoromethylphenyl)-5-methylamino-4-trifluoroacetylpyrazole;

3-cyano-1-(2,6-dichloro-4-trifluoromethylphenyl)-5-(prop-2-enylamino)-4-trifluoroacetylpyrazole;

3-cyano-1-(2,6-dichloro-4-trifluoromethylphenyl)-5-phenylmethylamino-4-trifluoroacetylpyrazole; and 3-cyano-1-(2,6-dichloro-4-trifluoromethylphenyl)-5-(prop-2-ylamino)-4-trifluoroacetylpyrazole.

14. A pharmaceutical, veterinary or agricultural parasiticidal formulation comprising a compound or salt as defined in claim 1, without proviso, in admixture with a compatible adjuvant, diluent or carrier.

15. A method of treating a parasitic infestation at a locus, which comprises treating the locus with an effective amount of a compound or salt according to claim 1, without proviso, or a formulation thereof.

16. A method of killing a parasite comprising administering an effective amount of a compound or salt as defined in claim 1, without proviso, or a formulation thereof, to said parasite or the vicinity thereof.

17. A process for the manufacture of a compound of formula (I) as defined in claim 1 comprising:

(a) where X is oxygen and $R^8$ is $CH_2R^9$ where $R^9$ is H or $C_{1-7}$ akyl optionally substituted with one or more halogen, hydration of a compound of the formula (II)

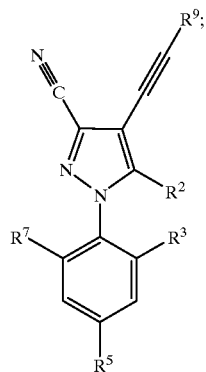

(II)

or (b) where X is oxygen, reacting the corresponding 4-iodopyrazoles with a lithiating agent, optionally in the presence of another base, optionally in the presence of cuprous bromide—dimethyl sulphide, followed by addition of an acylating species $R^8COZ$, where Z is a suitable leaving group such as $OCOR^8$, dialkylamine or halogen;

or (c) where X is oxygen, oxidation of the corresponding alcohol (III)

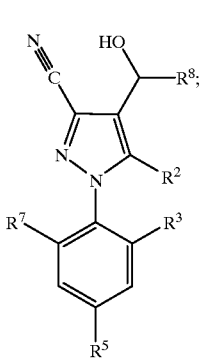

(III)

or (d) where X is oxygen and $R^8$ is H, oxidative cleavage of the corresponding 4-ethenylpyrazoles of formula (IV)

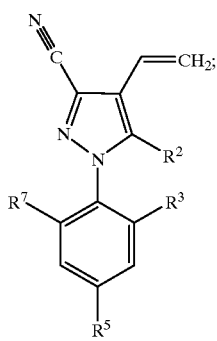

(IV)

or (e) where X is NOY, condensation of the corresponding compounds of formula (I) where X is O with a reagent of formula $YONH_2$, or a salt thereof, optionally in the presence of a suitable base;

or (f) where X is NOY and Y is $C_{1-6}$ alkyl optionally substituted with one or more halogen, alkylation of the corresponding compounds of formula (I) where X is NOY and Y is H with a suitable optionally substituted alkylating agent, optionally in the presence of a base;

or (g) where $R^2$ is H, reaction of the corresponding compounds of formula (I) where $R^2$ is $NH_2$ with an alkyl nitrite;

or (h) where $R^2$ is Cl, Br or I, diazotisation of the corresponding compound where $R^2$ is $NH_2$ in the presence of a source of chloride, bromide or iodide;

or (i) where $R^2$ is F, reacting the compound of formula (I) where $R^2$ is chloride, bromide or iodide with a fluoride source;

or (j) where $R^2$ is $C_{1-6}$ alkyl optionally substituted with one or more halogen, alkylation, with a suitable alkylating agent, of a 5-lithiopyrazole of formula (V)

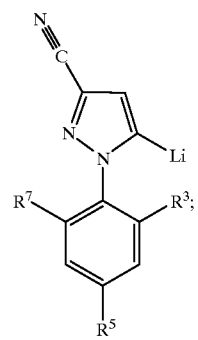

(V)

or (k) where $R^2$ is NH($C_{1-6}$ alkyl optionally substituted with one or more halogen), NH(allyl optionally substituted with one or more halogen), NH(benzyl optionally substituted with one or more halogen) or $NHSCF_3$, by reacting a compound of formula (I) where $R^2$ is $NH_2$ with the corresponding halide;

or (l) conversion of a compound of formula (I) into a pharmaceutically or veterinarily acceptable salt thereof, where unless specified otherwise, the substituents are as defined in claim 1.

18. The formulation of claim 14, wherein the compound or salt is the compound or salt as defined in claim 1.

19. The method of claim 15, wherein the compound or salt is the compound or salt as defined in claim 1.

20. The method of claim 16, wherein the compound or salt is the compound or salt as defined in claim 1.

* * * * *